United States Patent
Nakagawa et al.

(10) Patent No.: US 10,793,817 B2
(45) Date of Patent: Oct. 6, 2020

(54) CELL CULTURE DEVICE

(71) Applicants: TOYODA GOSEI CO., LTD., Kiyosu-shi, Aichi-ken (JP); National University Corporation Yamagata University, Yamagata-shi, Yamagata (JP)

(72) Inventors: Hiroyuki Nakagawa, Kiyosu (JP); Seitaro Taki, Kiyosu (JP); Hisashi Mizuno, Kiyosu (JP); Toshiyuki Hagiyama, Kiyosu (JP); Atsuki Yoshimura, Kiyosu (JP); Yasuhiko Shinoda, Kiyosu (JP); Yasuhiko Ogisu, Kiyosu (JP); Masaru Tanaka, Yonezawa (JP); Chikako Sato, Yonezawa (JP)

(73) Assignees: TOYODA GOSEI CO., LTD., Aichi-pref. (JP); National University Corporation Yamagata University, Yamagata-shi (JP)

( * ) Notice: Subject to any disclaimer, the term of this patent is extended or adjusted under 35 U.S.C. 154(b) by 153 days.

(21) Appl. No.: 15/306,635

(22) PCT Filed: Mar. 23, 2015

(86) PCT No.: PCT/JP2015/001611
§ 371 (c)(1),
(2) Date: Oct. 25, 2016

(87) PCT Pub. No.: WO2015/166625
PCT Pub. Date: Nov. 5, 2015

(65) Prior Publication Data
US 2017/0044480 A1 Feb. 16, 2017

(30) Foreign Application Priority Data
Apr. 28, 2014 (JP) ................. 2014-092490

(51) Int. Cl.
*C12M 1/12* (2006.01)
*C12M 3/00* (2006.01)

(52) U.S. Cl.
CPC ............ *C12M 25/02* (2013.01); *C12M 23/06* (2013.01); *C12M 23/48* (2013.01)

(58) Field of Classification Search
CPC ...... C12M 23/06; C12M 23/48; C12M 25/02; C12M 3/04
See application file for complete search history.

(56) References Cited

U.S. PATENT DOCUMENTS

| 5,759,851 A | 6/1998 | Mathus | |
|---|---|---|---|
| 2003/0215940 A1* | 11/2003 | Lacey | ................. B01L 3/50853 435/305.2 |
| 2013/0280807 A1 | 10/2013 | Takezawa et al. | |

FOREIGN PATENT DOCUMENTS

| CN | 103261394 A | 8/2013 |
|---|---|---|
| JP | H11-510394 A | 9/1999 |

(Continued)

OTHER PUBLICATIONS

Office Action dated Feb. 23, 2018 issued in corresponding CN patent application No. 201580022266.9 (and English translation).

(Continued)

*Primary Examiner* — Gautam Prakash
*Assistant Examiner* — Lydia Edwards
(74) *Attorney, Agent, or Firm* — Posz Law Group, PLC (57) ABSTRACT

A cell culture device comprises a first inner cylinder formed in a tubular shape, a cell culture membrane placed to cover over an entire one end of the first inner cylinder and configured to be folded down toward an outer surface of the first inner cylinder along an outer circumference at the one end of the first inner cylinder, and an outer cylinder formed in a tubular shape, configured to place the first inner cylinder inside thereof such that a height direction of the outer (Continued)

cylinder is identical with a height direction of the first inner cylinder, and provided with a first slit in an area overlapping with at least the one end of the first inner cylinder to be extended in the height direction, wherein the cell culture membrane is held between an inner wall surface of the outer cylinder and the outer surface of the first inner cylinder.

11 Claims, 9 Drawing Sheets

(56) References Cited

FOREIGN PATENT DOCUMENTS

| JP | 2005-137319 A | | 6/2005 |
|---|---|---|---|
| JP | 2005-348736 A | | 12/2005 |
| JP | 2005348736 A | * | 12/2005 |
| JP | 2006-304734 A | | 11/2006 |
| JP | 2007-167002 A | | 7/2007 |
| JP | 2012-115262 A | | 6/2012 |
| JP | 2013-230090 A | | 11/2013 |

OTHER PUBLICATIONS

International Search Report of the International Searching Authority dated Jun. 23, 2015 for the corresponding international application No. PCT/JP2015/001611 (and English translation).

* cited by examiner

CELL CULTURE DEVICE

CROSS REFERENCE TO RELATED APPLICATION APPLICATIONS

The present application is the U.S. national phase of International Patent Application No. PCT/JP2015/001611 filed on Mar. 23, 2015 and claims priority from Japanese Patent Application No. 2014-92490 filed on Apr. 28, 2014, the entirety of disclosure of which is hereby incorporated by reference into this application.

TECHNICAL FIELD

The present disclosure relates to a cell culture device.

BACKGROUND ART

The cell culture technology has recently been drawn attention as the useful technique in various fields such as drug development and regenerative medicine. A cell culture membrane that is a base material serving as the scaffold of cells is generally used for culturing scaffold-based cells. A proposed cell culture device provided with such a cell culture membrane may be, for example, configured such that the cell culture membrane is placed between two ring-shaped members that have concave-convex shapes engaging with each other and is held by placing an outer periphery of the cell culture membrane between the areas of the concave-convex shapes (for example, Patent Literature 1).

CITATION LIST

Patent Literature

PTL 1: JP 2005-348736A
PTL 2: JP H11-510394A

SUMMARY

Technical Problem

The cell culture membrane, however, generally has a thickness of approximately several µm to several tens µm. The concave-convex shapes of the ring-shaped members with the outer periphery of the cell culture membrane placed therebetween as described above needs to have sufficiently high dimensional accuracy, in order to securely hold such a thin cell culture membrane. The demand for such high dimensional accuracy is likely to cause complication of the manufacturing process of the cell culture device and increase the cost. There is accordingly a demand for a cell culture device that enables a cell culture membrane to be held with sufficiently high reliability, while suppressing demands for the dimensional accuracy of the components of the cell culture device.

Solution to Problem

In order to solve at least one of the problems described above, the disclosure may be implemented by aspects described below.

(1) According to one aspect of the disclosure, there is provided a cell culture device. This cell culture device comprises: a first inner cylinder formed in a tubular shape; a cell culture membrane placed to cover over an entire one end of the first inner cylinder and configured to be folded down toward an outer surface of the first inner cylinder along an outer circumference at the one end of the first inner cylinder; and an outer cylinder formed in a tubular shape, configured to place the first inner cylinder inside thereof such that a height direction of the outer cylinder is identical with a height direction of the first inner cylinder, and provided with a first slit in an area overlapping with at least the one end of the first inner cylinder to be extended in the height direction, wherein the cell culture membrane is placed and held between an inner wall surface of the outer cylinder and the outer surface of the first inner cylinder.

In the cell culture device of this aspect, the first slit is provided in the area overlapping with the one end of the first inner cylinder to be extended in the height direction. The cell culture membrane is placed and held between the inner wall surface of the outer cylinder and the outer surface of the first inner cylinder. This configuration enables the cell culture membrane to be held with sufficiently high reliability, while suppressing the demands for the dimensional accuracy of the respective members. This results in suppressing complication of the manufacturing process of the cell culture device and reducing an increase in cost.

(2) In the cell culture device of the above aspect, the first slit may be formed along the height direction in the entire outer cylinder. This configuration of the cell culture device facilitates the operation of inserting the first inner cylinder with the cell culture membrane placed at the one end into the outer cylinder.

(3) In the cell culture device of the above aspect, the outer cylinder may include a first grip portion provided at an end that is nearer to the one end of the first inner cylinder out of two ends of the first inner cylinder by linking different locations on an outer circumference of an opening at the end such as to cross the opening at the end.

This configuration enables the cell culture device to be suspended by holding the grip portion. This accordingly facilitates the operation for handling the cell culture device.

(4) The cell culture device of the above aspect may further comprise a second inner cylinder formed in a tubular shape such that a height direction of the second inner cylinder is identical with the height direction of the first inner cylinder and placed in the outer cylinder to come into contact with the first inner cylinder via the cell culture membrane on a side of the one end of the first inner cylinder.

The second inner cylinder suppresses cells from flowing out of the cell culture device through the first slit in the process of seeding the cells onto the surface of the cell culture membrane exposed to outside of the first inner cylinder. This accordingly improves the accuracy in number of cells to be seeded.

(5) In the cell culture device of the above aspect, the second inner cylinder may be configured to be slidable in the height direction in the outer cylinder by applying a force in the height direction and to be held at a slid position.

This configuration enables the air remaining on the surface of the cell culture membrane on which cells are seeded to be readily removed through the first slit when the second inner cylinder is slit to be away from the cell culture membrane and the cell culture device is turned upside down after the cells are seeded on the cell culture membrane exposed to inside of the second inner cylinder.

(6) In the cell culture device of the above aspect, the first slit may be formed in the outer cylinder to be extended from a position where the one end of the first inner cylinder comes into contact with the outer cylinder toward a direction away from the first inner cylinder in the height direction.

This configuration enables the air remaining on the surface of the cell culture membrane on which cells are seeded to be readily removed through the first slit, when the cell culture device is turned upside down after the cells are seeded on the surface of the cell culture membrane exposed to outside of the first inner cylinder.

(7) In the cell culture device of the above aspect, the first inner cylinder may include a second grip portion provided at other end out of the two ends of the first inner cylinder by linking different locations on an outer circumference of an opening at the other end such as to cross the opening at the other end.

This configuration enables the cell culture device to be suspended by holding the second grip portion, when the cell culture device is placed in such a direction that the other end of the first inner cylinder faces upward in the vertical direction. This accordingly facilitates the operation for handling the cell culture device.

(8) In the cell culture device of the above aspect, the first grip portion may be formed from two line segments that are arranged to cross each other in a neighborhood on an axial line of the first inner cylinder.

This configuration enables the cell culture membrane to be readily kept in the horizontal position stably when the first grip portion or the second grip portion is held to suspend the cell culture device. This accordingly suppresses an undesired external stimulus (noise) or the like on the cells cultured on the cell culture membrane.

(9) In the cell culture device of the above aspect, the second grip portion may be formed from two line segments that are arranged to cross each other in the neighborhood on the axial line of the first inner cylinder.

This configuration enables the cell culture membrane to be readily kept in the horizontal position stably when the first grip portion or the second grip portion is held to suspend the cell culture device. This accordingly suppresses an undesired external stimulus (noise) or the like on the cells cultured on the cell culture membrane.

(10) In the cell culture device of the above aspect, the first inner cylinder may include a second slit provided at a position that overlaps with the first slit provided in the outer cylinder to be extended in the height direction from the one end of the first inner cylinder; and a pair of membrane supports provided at positions which overlap with the first slit provided in the outer cylinder and between which the second slit is open at the one end of the first inner cylinder, such as to be extended outward in a radial direction of the first inner cylinder via the first slit to outside of the outer cylinder.

This configuration enables the air remaining on the rear side of the surface of the cell culture membrane on which cells are seeded to be removed through the first slit and the second slit in the process of seeding the cells on the surface of the cell culture membrane that is exposed to outside of the first inner cylinder.

(11) In the cell culture device of the above aspect, the first inner cylinder may have a concave-convex shape that is provided at a position to come into contact with the cell culture membrane on an outer surface near to the one end of the first inner cylinder.

This configuration enhances the holding force for holding the cell culture membrane placed between the first inner cylinder and the outer cylinder.

The disclosure may be implemented by any of various aspects other than the above device, for example, an outer cylinder for the cell culture device, a method of manufacturing the cell culture device, a method of holding a cell culture membrane and a cell culture method using the cell culture device.

Advantageous Effects

In the cell culture device of the disclosure, the first slit is provided in the area overlapping with the one end of the first inner cylinder to be extended in the height direction. The cell culture membrane is placed and held between the inner wall surface of the outer cylinder and the outer surface of the first inner cylinder. This configuration enables the cell culture membrane to be held with sufficiently high reliability, while suppressing the demands for the dimensional accuracy of the respective members. This results in suppressing complication of the manufacturing process of the cell culture device and reducing an increase in cost.

DESCRIPTION OF EMBODIMENTS

A. First Embodiment

Figure 1A:
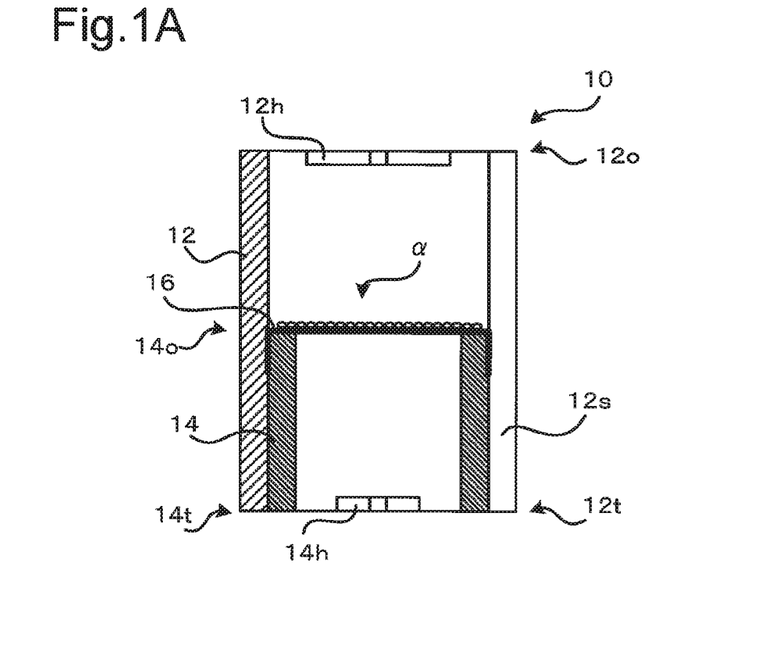
FIGS. 1A and 1B are sectional schematic diagrams illustrating the configuration of a cell culture device.
Figure 1B:
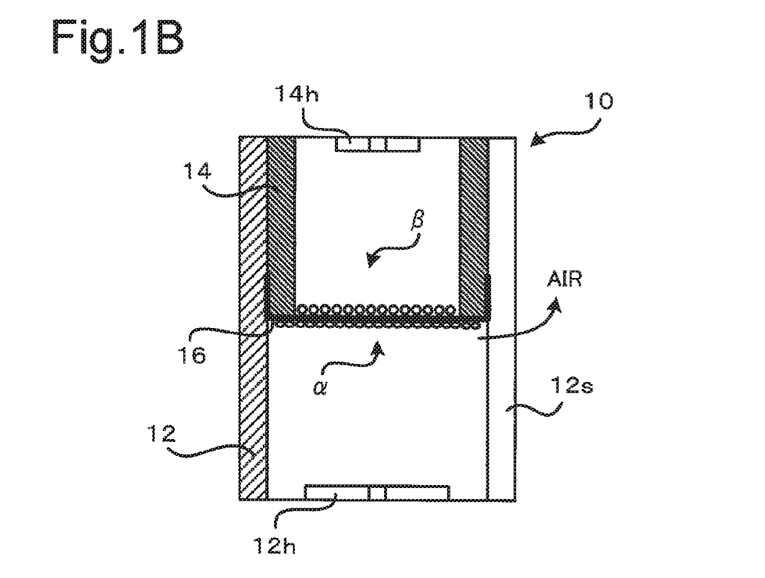
Figure 2:
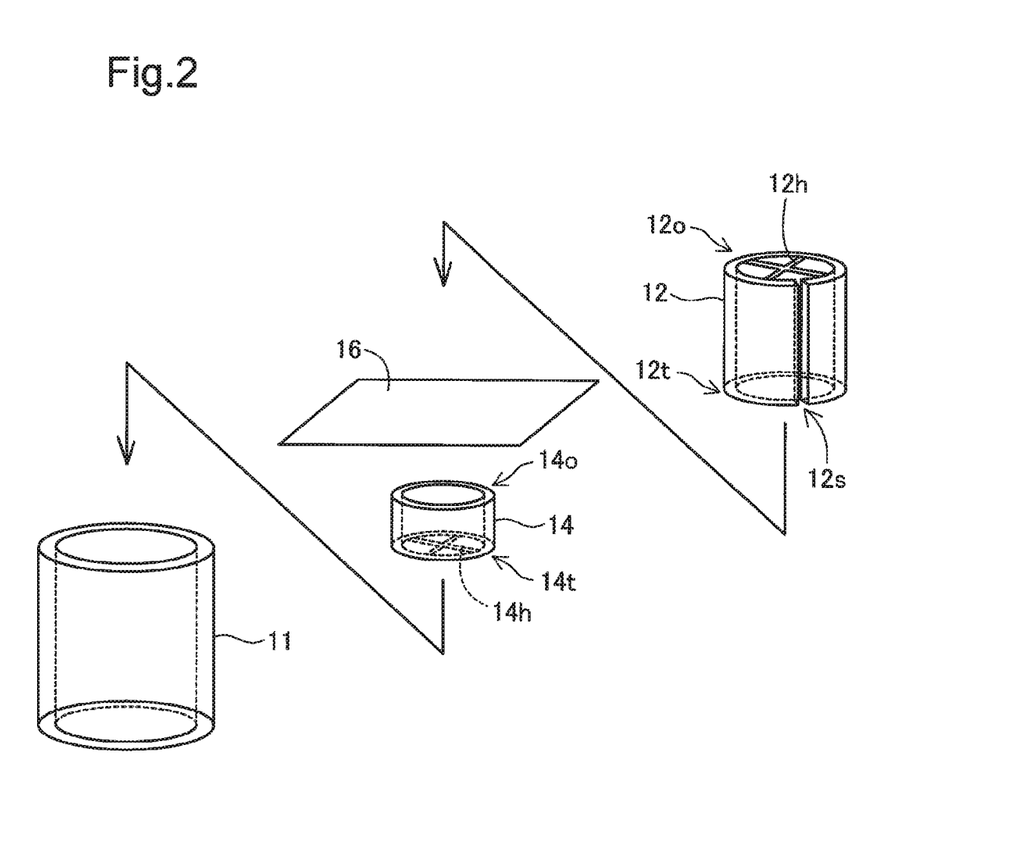
FIG. 2 is an exploded perspective view illustrating assembly of the cell culture device.
Figure 3:
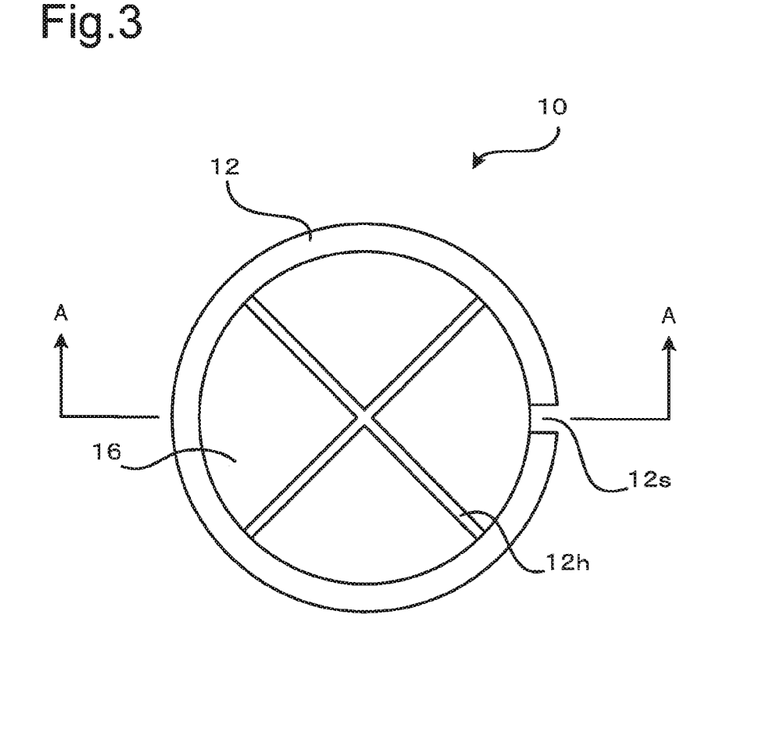
FIG. 3 is a top view illustrating the cell culture device.

FIGS. 1A and 1B are sectional schematic diagrams illustrating the configuration of a cell culture device 10 according to a first embodiment of the disclosure. FIG. 2 is an exploded perspective view illustrating assembly of the cell culture device 10. FIG. 3 is a top view illustrating the cell culture device 10. The position of the section shown in FIGS. 1A and 1B is shown as A-A section in FIG. 3. The cell culture device 10 includes an outer cylinder 12, a first inner cylinder 14 and a cell culture membrane 16.

The outer cylinder 12 is a tubular member and has a first slit $12s$ extended in a height direction from one end $12o$ to the other end $12t$. The outer cylinder 12 has a first grip portion $12h$ provided at the one end $12o$ by linking different locations on the outer circumference of an opening at this one end $12o$ with each other such as to cross the opening. More specifically the first grip portion $12h$ is formed from two line segments that are arranged to cross each other on an axial line of the first inner cylinder 14, i.e., that are arranged in a cross shape in the top view (as shown in FIG. 2 and FIG. 3). The outer cylinder 12 may be formed from, for example, a resin material or rubber. The outer cylinder 12 has the first slit $12s$ extended in the height direction and may thus be formed from a material that is elastically deformable in a radial direction. The cell culture membrane 16 is placed and held between the outer cylinder 12 and the first inner cylinder 14 as described later. The outer cylinder 12 may thus be formed from a material that produces a sufficient holding force inward in the radial direction when the outer cylinder 12 is elastically deformed outward in the radial direction such as to hold the cell culture membrane 16 placed between the outer cylinder 12 and the first inner cylinder 14.

The first inner cylinder 14 is a tubular member formed to have a lower height than the height of the outer cylinder 12. The cell culture membrane 16 is placed at one end 14$o$ of the first inner cylinder 14, and a second grip portion 14$h$ that is similar to the first grip portion 12$h$ provided in the outer cylinder 12 is provided at the other end 14$t$ of the first inner cylinder 14. The first inner cylinder 14 may be formed from, for example, a resin material or glass. The cell culture membrane 16 is placed and held between the outer cylinder 12 and the first inner cylinder 14 as described later. The first inner cylinder 14 may thus be formed from a material that provides such rigidity that is unlikely to substantially deform the first inner cylinder 14 under application of a force inward in the radial direction from the inner wall surface of the outer cylinder 12.

The cell culture device 10 is soaked in a culture solution when being used for cell culture as described later. The outer cylinder 12 and the first inner cylinder 14 may thus be formed from a material that does not cause a component such as metal ion likely to affect cultured cells to be substantially eluted into the culture solution. It is also desired that the outer cylinder 12 and the first inner cylinder 14 are formed from a material having a specific gravity that does not cause the cell culture device 10 to be floated in the culture solution. When the outer cylinder 12 and the first inner cylinder 14 are formed from a resin, the resin may be selected from the group consisting of, for example, polyethylene, polypropylene (PP), silicone resin, polytetrafluoroethylene (PTFE), polyethylene terephthalate (PET) and poly(methyl methacrylate) (PMMA).

The cell culture membrane 16 is a membrane serving as a scaffold of cultured cells when being used for cell culture. The cell culture membrane 16 may be a membrane selected from the group consisting of, for example, a polyurethane membrane, a cellulose membrane, a collagen membrane, an amniotic membrane and a hyaluronic acid membrane. According to this embodiment, the cell culture device 10 is used with the cell culture membrane 16 folded down and held between the outer cylinder 12 and the first inner cylinder 14. The cell culture membrane 16 may accordingly have elasticity and strength to withstand such folding and holding. When a porous membrane having a large number of pores that are formed to pass through the membrane in the thickness direction is used as the cell culture membrane 16, different types of cells may be cultured on the respective surfaces for the purpose of analysis of the interactions between the different types of cells as described later. It is especially preferable to use a porous polyurethane membrane for the cell culture membrane 16, in terms of easily forming the through holes that pass through the membrane in the thickness direction and providing the high elasticity and high strength.

A porous polyurethane membrane used as the cell culture membrane 16 may be manufactured by, for example, the following procedure. An uncured polyurethane raw material including a polyol such as polyether polyol, an isocyanate such as an aromatic isocyanate, and a diluting agent is provided first. A layer of the provided uncured polyurethane raw material is subsequently formed on a base plate. A polyurethane porous membrane is then obtained by curing the layer of the polyurethane raw material with supplying the water vapor to the layer of the uncured polyurethane raw material.

A concrete method employed to supply the water vapor to the layer of the uncured polyurethane raw material may, for example, place the layer of the uncured polyurethane raw material on the base plate in a closed container containing water, such that an exposed surface of the layer of the uncured polyurethane raw material is arranged to face water. The inside of the closed container is maintained at a predetermined temperature to be kept at a saturated vapor pressure. The water vapor is accordingly supplied through the surface of the layer of the uncured polyurethane raw material, and a reaction proceeds between the isocyanate in the polyurethane raw material and the water vapor to produce carbon dioxide. A curing reaction also proceeds between the polyol and the isocyanate. As described above, the porous polyurethane membrane is obtained by foaming polyurethane in the middle of curing. The shape of the porous polyurethane membrane may be controlled by adjusting conditions selected among the reaction temperature and the reaction time in the curing reaction accompanied with supply of the water vapor described above, the amount of water vapor supplied during curing and the composition of the polyurethane raw material.

A method of assembling the cell culture device 10 using the outer cylinder 12, the first inner cylinder 14 and the cell culture membrane 16 is shown in FIG. 2. In the process of assembling the cell culture device 10, the cell culture membrane 16 is first placed on the one end 14$o$ of the first inner cylinder 14 (end without the second grip portion 14$h$). The cell culture membrane 16 is shown as a rectangular shape in FIG. 2 but may be formed in a different shape. The cell culture membrane 16 may have any size that is sufficiently larger than the ends (cross sections) of the first inner cylinder 14 to cover over the entire one end 14$o$ of the first inner cylinder 14 and that enables the cell culture membrane 16 to be held with high reliability when the peripheral part of the cell culture membrane 16 is placed between the outer cylinder 12 and the first inner cylinder 14.

The other end 12$t$ of the outer cylinder 12 (end without the first grip portion 12$h$) is then mounted from the one end 14$o$-side onto the first inner cylinder 14. The cell culture membrane 16 is accordingly folded down along the outer circumference at the one end 14$o$ of the first inner cylinder 14. The peripheral part of the cell culture membrane 16 that is on the outer circumferential side of the folding position is accordingly placed and held between the outer surface of the first inner cylinder 14 and the inner wall surface of the outer cylinder 12. According to this embodiment, the outer cylinder 12 is mounted such that the other end 12$t$ of the outer cylinder 12 overlaps with the other end 14$t$ of the first inner cylinder 14 (end with the second grip portion 14$h$) (as shown in FIG. 1A).

The inner diameter of the outer cylinder 12 is made smaller than the outer diameter of the first inner cylinder 14, prior to such mounting. In the process of mounting the outer cylinder 12 outside of the first inner cylinder 14 to place the first inner cylinder 14 and the cell culture membrane 16 in the outer cylinder 12, the outer cylinder 12 is spread out to open the first slit 12$s$ and is elastically deformed outward in the radial direction. This produces a holding force inward in the radial direction from the outer cylinder 12 toward the first inner cylinder 14 and causes the outer cylinder 12 and the first inner cylinder 14 to come into close contact with each other via, the cell culture membrane 16 without any clearance. As a result, the cell culture membrane 16 is held between the outer cylinder 12 and the first inner cylinder 14. In the process of mounting the outer cylinder 12, the outer cylinder 12 may be mounted outside of the first inner cylinder 14 in the state that the inner diameter of the outer cylinder 12 is expanded in advance to be approximately equal to or slightly larger than the outer diameter of the inner cylinder 14. The diameter of the outer cylinder 12 may subsequently be reduced by its elastic restoring force, such that the cell culture membrane 16 is held between the outer cylinder 12 and the inner cylinder 14. The outer cylinder 12 mounted outside of the first inner cylinder 14 as described above holds the inner cylinder 14 with such a holding force that does not change the position of the first inner cylinder 14 relative to the outer cylinder 12 even when the cell culture device 10 is turned upside down as described later.

When the assembled cell culture device 10 is used for cell culture, the cell culture device 10 is placed in a well 11 of a plate for cell culture (shown in FIG. 2), and the well 11 is filled with a culture solution.

FIG. 1A schematically illustrates the state that cells α are seeded on one surface of the cell culture membrane 16 (surface exposed to outside of the first inner cylinder 14). A culture solution and a well 11 of a plate for cell culture are omitted from the illustration of FIGS. 1A and 1B. A procedure of seeding the cells α on one surface of the cell culture membrane 16 may supply a predetermined amount of the cells α into a space formed above the one surface of the cell culture membrane 16 in the outer cylinder 12 in the state that the cell culture device 10 is soaked in the culture solution such that the one end 12o of the outer cylinder 12 is located on the upper side in the vertical direction.

FIG. 1B illustrates the state that different cells β from the cells α are additionally seeded on the other surface of the cell culture membrane 16 (surface exposed to inside of the first inner cylinder 14). A procedure of seeding the cells β may turn the cell culture device 10 upside down after the cells α are seeded as shown in FIG. 1A and cultured for a predetermined time period and may supply a predetermined amount of the cells β into a space formed above the other surface of the cell culture membrane 16 in the outer cylinder 12 and the first inner cylinder 14. Using a porous membrane having a large number of through holes that pass through in the thickness direction as the cell culture membrane 16 enables different types of cells to be cultured on the respective surfaces as described above for the purpose of analysis of the interactions between the different types of cells.

In the cell culture device 10 of the embodiment having the above configuration, the outer cylinder 12 with the first slit 12s extended in the height direction is mounted outside of the first inner cylinder 14 from the side where the cell culture membrane 16 is placed. This produces the holding force inward in the radial direction from the outer cylinder 12 toward the first inner cylinder 14 and causes the cell culture membrane 16 to be placed and held between the outer cylinder 12 and the first inner cylinder 14. This configuration enables the cell culture membrane 16 to be held with sufficiently high reliability while suppressing the demands for the dimensional accuracy of the respective members. This results in suppressing complication of the manufacturing process of the cell culture device and reducing an increase in cost.

The configuration of the cell culture device 10 according to the embodiment also simplifies the assembling operation of the cell culture device 10. More specifically, the cell culture device 10 may be assembled by a simple operation that places the cell culture membrane 16 on the one end 14o of the first inner cylinder 14 and mounts the outer cylinder 12 outside of the first inner cylinder 14 and the cell culture membrane 16 while folding down the cell culture membrane 16 along the opening at the one end 14o of the first inner cylinder 14.

Especially, in the cell culture device 10 of the embodiment, the first slit 12s is formed along the entire height of the outer cylinder 12. This configuration facilitates the operation of inserting the first inner cylinder 14 with the cell culture membrane 16 placed at an end thereof into the outer cylinder 12.

The cell culture device 10 of the embodiment is provided with the first grip portion 12h of the outer cylinder 12 and the second grip portion 14h of the first inner cylinder 14, each being configured by linking different locations on the outer circumference of an opening at an end of the outer cylinder 12 or at an end of the first inner cylinder 14 with each other such as to cross the opening. This configuration enables the cell culture device 10 to be suspended by holding the grip portion 12h or the grip portion 14h, in order to place the cell culture device 10 into the well 11 or in order to pull up the cell culture device 10 from the well 11. This accordingly facilitates the operation for handling the cell culture device 10.

Specifically, according to this embodiment, each of the first grip portion 12h and the second grip portion 14h is formed from two line segments that are arranged to cross each other on the axial line of the first inner cylinder 14. The configuration of holding the cell culture device 10 at the intersection of the two line segments enables the cell culture device 10 to be readily held in the vicinity immediately above the center of gravity of the cell culture device 10. As a result, this causes the cell culture membrane 16 to be readily kept in the horizontal position when the cell culture device 10 is suspended, and readily suppresses an undesired external stimulus (noise) or the like on the cells that are cultured on the cell culture membrane 16.

The location "on the axial line of the first inner cylinder 14" where the intersection of the two line segments is located with regard to the first grip portion 12h and the second grip portion 14h includes the vicinity on the axial line of the first inner cylinder 14. More specifically, when the outer cylinder 12 and the first inner cylinder 14 are formed in cylindrical shape, the configuration that "the intersection is located on the axial line of the first inner cylinder 14" includes a configuration that the intersection is included in the range of a concentric circle of the first inner cylinder 14 that has a diameter of one tenth of the inner circumference of the first inner cylinder 14, in a plane that includes the intersection and is perpendicular to the axial line of the first inner cylinder 14. As described later, the first inner cylinder 14 may be formed in a tubular shape other than the cylindrical shape. In this case, the configuration that "the intersection is located on the axial line of the first inner cylinder 14" includes a configuration that the intersection is included in such a range that the inner circumference of the first inner cylinder 14 is reduced to one tenth about the center of gravity kept unchanged, in the plane that includes the intersection and is perpendicular to the axial line of the first inner cylinder 14. The plane perpendicular to the axial line of the first inner cylinder 14 preferably has a rotationally symmetrical shape, in terms of keeping the cell culture membrane 16 in the horizontal position and suppressing an undesired external stimulus (noise) or the like on the cells.

Additionally in the cell culture device 10 of the embodiment, the first slit 12s formed in the outer cylinder 12 is extended from the location where the one end 14t of the first inner cylinder 14 is arranged to overlap with the outer cylinder 12 toward a direction away from the first inner cylinder 14 in the height direction. Accordingly the space above one surface of the cell culture membrane 16 (culture surface of the cells α seeded first) in the outer cylinder 12 communicates with outside of the outer cylinder 12 via the first slit 12s in the vicinity of the culture surface of the cells α. This configuration enables the air to be readily removed from the culture surface of the cells α through the first slit 12s when the cell culture device 10 is inverted. The state of air removal is shown by an arrow in FIG. 1B. This suppresses a problem caused by the air remaining on the culture surface of the cells α seeded first (for example, failure in exposure of the cells α to the culture solution).

The cell culture device 10 of the embodiment uses a porous membrane having a large number of through holes that pass through in the thickness direction, as the cell culture membrane 16 and enables cells to be cultured on the respective surfaces of the cell culture membrane. This configuration enables the cells to be readily seeded on the respective surfaces of the cell culture membrane 16 by the simple operation of inverting the cell culture device 10.

B. Second Embodiment

Figure 4A:
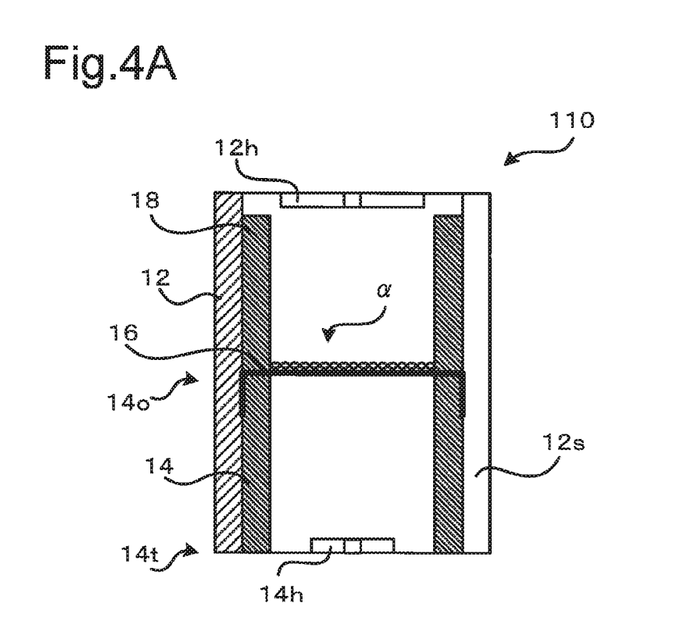
FIGS. 4A and 4B are sectional schematic diagrams illustrating the configuration of another cell culture device.
Figure 4B:
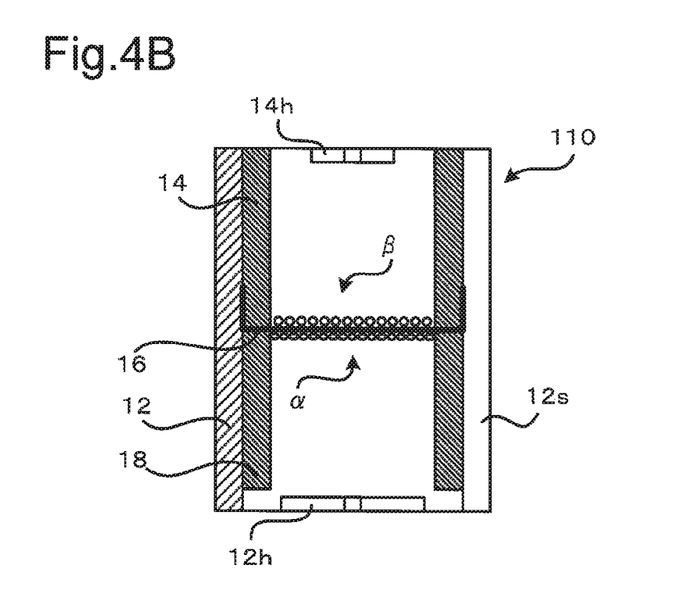
Figure 5:
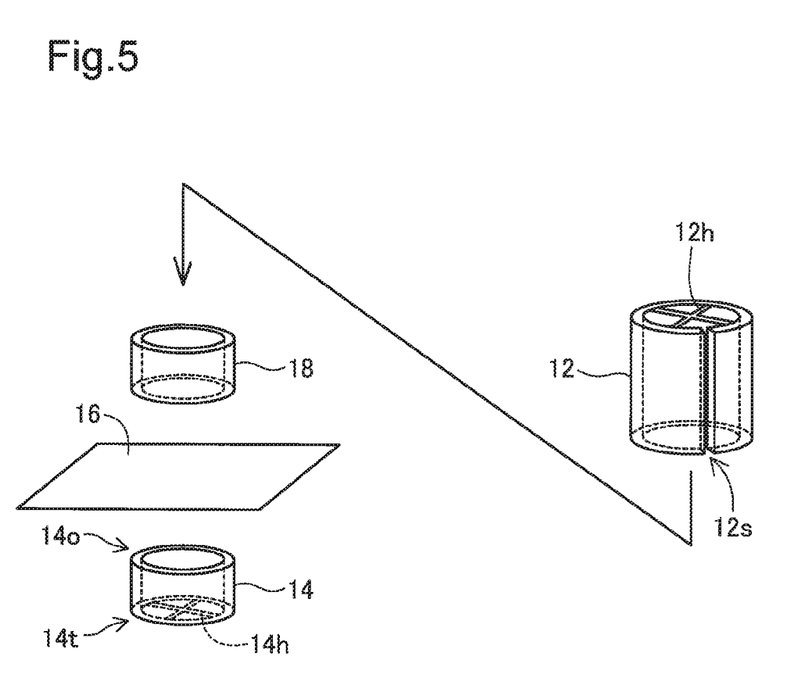
FIG. 5 is an exploded perspective view illustrating assembly of the cell culture device.

FIGS. 4A and 4B are sectional schematic diagrams illustrating the configuration of a cell culture device 110 according to a second embodiment of the disclosure, like FIGS. 1A and 1B. FIG. 5 is an exploded perspective view illustrating assembly of the cell culture device 110. In the description below, the like components to those of the cell culture device 10 of the first embodiment are expressed by the like reference numbers and are not described in detail. The cell culture device 110 includes a second inner cylinder 18, in addition to an outer cylinder 12, a first inner cylinder 14 and a cell culture membrane 16.

The second inner cylinder 18 is a tubular member formed to have a similar outer diameter to the outer diameter of the first inner cylinder 14 and a lower height than the height of the outer cylinder 12. The second inner cylinder 18 may be formed from a similar material to that of the first inner cylinder 14. As shown in FIGS. 4A and 4B, the second inner cylinder 18 has a height direction that is identical with the height direction of the first inner cylinder 14 and is placed in the outer cylinder 12 such as to come into contact with the first inner cylinder 14 via the cell culture membrane 16 on one end 14o-side of the first inner cylinder 14. The second inner cylinder 18 is formed to have the outer diameter that does not exceed the outer diameter of the first inner cylinder 14, in order not to reduce the holding force of the first inner cylinder 14 and the outer cylinder 12 for holding the cell culture membrane 16.

As shown in FIG. 5, the difference from the first embodiment in the process of assembling the cell culture device 110 is additionally placing the second inner cylinder 18 on the cell culture membrane 16 after placing the cell culture membrane 16 on the one end 14o of the first inner cylinder 14 (end without the second grip portion 14h). The outer cylinder 12 is subsequently mounted outside of the first inner cylinder 14 and the second inner cylinder 18 that are arranged to hold the cell culture membrane 16 placed therebetween, in a mounting direction relative to the first inner cylinder 14 similar to the mounting direction in the first embodiment.

FIG. 4A illustrates the state that cells α are seeded on one surface of the cell culture membrane 16, like FIG. 1A. FIG. 4B illustrates the state that the cell culture device 110 of FIG. 4A is inverted and different cells β from the cells α are additionally seeded on the other surface of the cell culture membrane 16, like FIG. 1B. According to this embodiment, the position of the second inner cylinder 18 relative to the outer cylinder 12 may be maintained even after inversion by adjusting the relationship between the outer diameter of the second inner cylinder 18 and the inner diameter of the outer cylinder 12 in the state that the first inner cylinder 14 is placed inside thereof, the surface roughness of the inner wall surface of the outer cylinder 12 and the outer surface of the second inner cylinder 18, and the weight of the second inner cylinder 18.

This configuration also provides the above advantageous effect of readily holding the cell culture membrane 16 by the presence of the first slit 12s provided in the outer cylinder 12, like the first embodiment. The second embodiment additionally uses the second inner cylinder 18. This suppresses the cells α supplied onto the cell culture membrane 16 from flowing out of the cell culture device 110 in the process of seeding the cells α This accordingly improves the accuracy in the number of cells to be seeded in the process of seeding the cells α.

C. Third Embodiment

Figure 6:
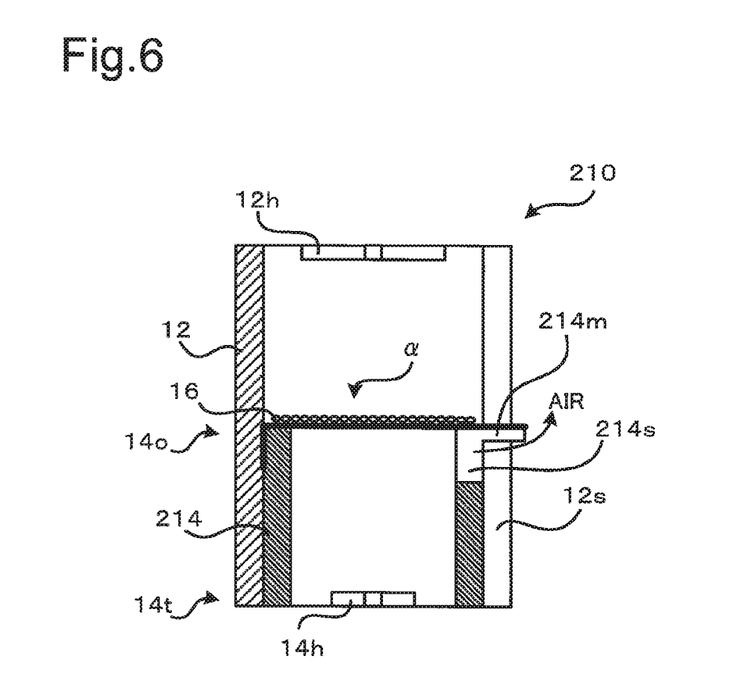
FIG. 6 is a sectional schematic diagram illustrating the configuration of another cell culture device.

FIG. 6 is a sectional schematic diagram illustrating the configuration of a cell culture device 210 according to a third embodiment of the disclosure, like FIGS. 1A and 1B. In the description below, the like components to those of the cell culture device 10 of the first embodiment are expressed by the like reference numbers and are not described in detail. The cell culture device 210 has a similar configuration to that of the cell culture device 10, except that a first inner cylinder 214 is provided in place of the first inner cylinder 14. The first inner cylinder 214 has a second slit 214s and a pair of membrane supports 214m.

Figure 7:
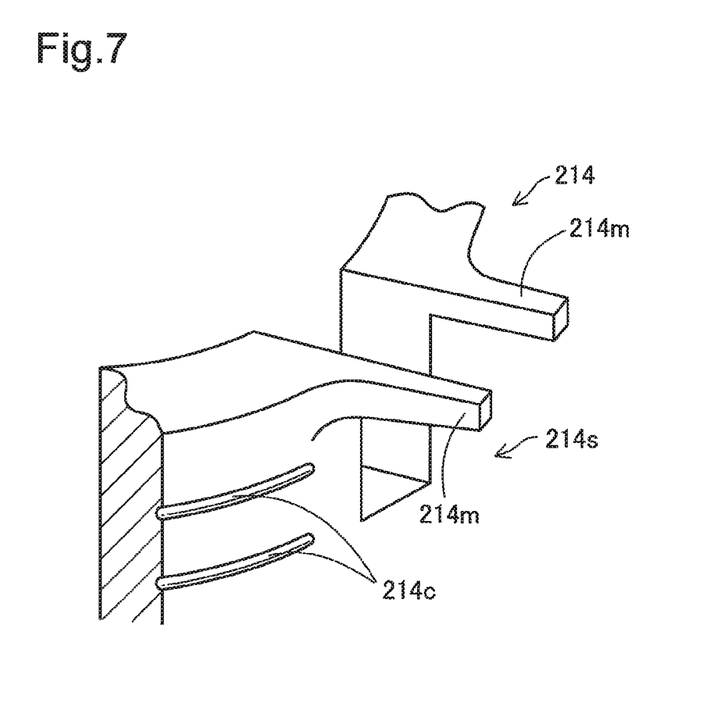
FIG. 7 is an enlarged perspective view illustrating part of a first inner cylinder.

FIG. 7 is an enlarged perspective view illustrating part of the first inner cylinder 214. The second slit 214s is formed in the first inner cylinder 214 to be extended in a height direction from one end 14o (end without the second grip portion 14h and with the cell culture membrane 16 placed thereon, as shown in FIG. 6). The pair of membrane supports 214m are provided at positions between which the second slit 214s is open on the one end 14o of the first inner cylinder 214, such as to be extended outward in a radial direction of the first inner cylinder 214. The first inner cylinder 214 is placed in the outer cylinder 12, such that the second slit 214s and the membrane supports 214m are arranged to overlap with the first slit 12s provided in the outer cylinder 12 and that the membrane supports 214m are extended through the first slit 12s to outside of the outer cylinder 12.

In the process of assembling the cell culture device 210, like the first embodiment, the cell culture membrane 16 is placed on the one end 14o of the first inner cylinder 214, and the other end 12t of the outer cylinder 12 (end without the first grip portion 12h) is mounted from this one end 14o-side. This folds down the cell culture membrane 16 along the outer circumference on the one end 14o of the first inner cylinder 214 and causes the peripheral part of the cell culture membrane 16 to be placed and held between the outer surface of the first inner cylinder 214 and the inner wall surface of the outer cylinder 12. The membrane supports 214m are provided on the first inner cylinder 214, so that the cell culture membrane 16 does not come into contact with the outer surface of the first inner cylinder 214 in the vicinity of the membrane supports 214m. As a result, the second slit 214s of the first inner cylinder 214 is not blocked by the cell culture membrane 16, and inside of the first inner cylinder 214 and outside of the outer cylinder 12 communicate with each other via the first slit 12s and the second slit 214s.

This configuration also provides the above advantageous effect of readily holding the cell culture membrane 16 by the presence of the first slit 12s provided in the outer cylinder 12, like the first embodiment. Additionally, according to the third embodiment, the second slit 214s and the membrane supports 214m provided in the first inner cylinder 214 cause inside of the first inner cylinder 214 and outside of the outer cylinder 12 to communicate with each other. This configuration enables the air remaining below the cell culture membrane 16 to be readily removed during cell culture in the state of FIG. 6. The state of air removal is shown by an arrow in FIG. 6. This suppresses a problem caused by the air remaining on the rear side of the culture surface in the process of seeding and culturing the cells α, like FIG. 1A. Additionally, according to this embodiment, the air is readily removed from the culture surface of the cells α through the first slit 12s like FIG. 1B in the process of turning the cell culture device 210 upside down from the state of FIG. 6 and culturing the cells β like FIG. 1B.

The second slit 214s is formed as a cut that is extended from the one end 14o of the first inner cylinder 214 to the position in the middle of the height of the first inner cylinder 214 according to the third embodiment but may be formed in a different shape. For example, the second slit 214s may be provided to be extended along the entire height of the first inner cylinder 214. The second slit 214s may be formed in any shape that enables the space in the vicinity immediately above the rear side of the culture surface of the cells α to communicate with outside.

According to the third embodiment, the first inner cylinder 214 also has two grooves 214c that are provided on an outer surface near to the one end 14o at a position in contact with the peripheral part of the cell culture membrane 16, as elongated concaves extended along the circumferential direction of the side face of the first inner cylinder 214. This configuration enhances the holding force for holding the peripheral part of the cell culture membrane 16 placed between the first inner cylinder 214 and the outer cylinder 12. The structure provided on the outer surface of the first inner cylinder 214 may be only the concaves like the two grooves described above, but may also be only convexes or a combination of concaves and convexes. The structure may be any concavo-convex shape that enhances the holding force for holding the cell culture membrane 16. Such a concavo-convex shape may be applied to any of the other embodiments and modifications.

D. Fourth Embodiment

Figure 8:
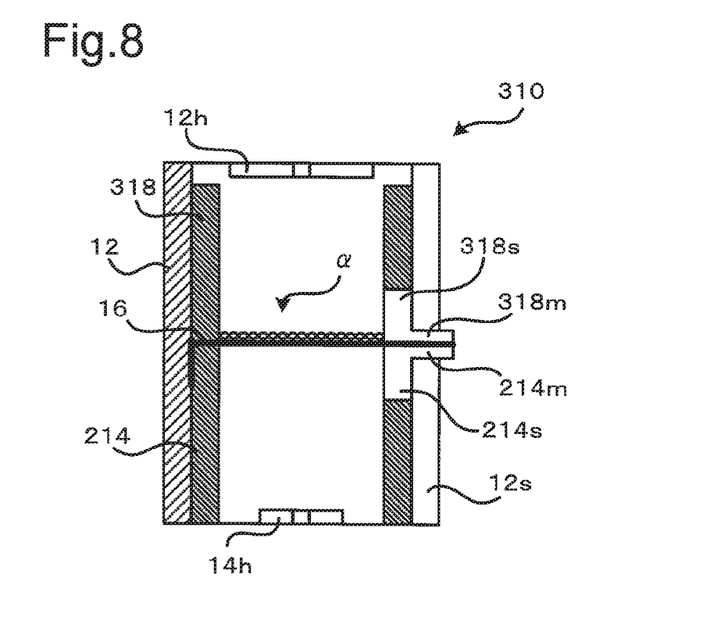
FIG. 8 is a sectional schematic diagram illustrating the configuration of another cell culture device.

FIG. 8 is a sectional schematic diagram illustrating the configuration of a cell culture device 310 according to a fourth embodiment of the disclosure, like FIGS. 1A and 1B. In the description below, the like components to those of first to the third embodiments are expressed by the like reference numbers and are not described in detail. The cell culture device 310 includes an outer cylinder 12, a first inner cylinder 214, a cell culture membrane 16 and a second inner cylinder 318.

The second inner cylinder 318 is placed to be laid on the first inner cylinder 214 such that their height directions are made identical with each other and to hold the cell culture membrane 16 placed between the end faces of the second inner cylinder 318 and the first inner cylinder 214. The second inner cylinder 318 has a shape plane symmetrical to the first inner cylinder 214 with respect to the cell culture membrane 16 as a plane of symmetry. More specifically; the second inner cylinder 318 is provided with a third slit 318s that is similar to the second slit 214s and with membrane supports 318s that are similar to the membrane supports 214m.

This configuration provides the similar advantageous effects to those of the cell culture device 210 of the third embodiment and additionally enables the air remaining immediately above the culture surface of the cells α to be readily removed through the third slit 318s when the cell culture device 310 is turned upside down after the cells α are seeded and cultured. The shape of the third slit 318s may not be necessarily the same shape as that of the second slit 214s but may be any shape that enables the space in the vicinity immediately above the culture surface of the cells α to communicate with outside.

E. Fifth Embodiment

Figure 9A:
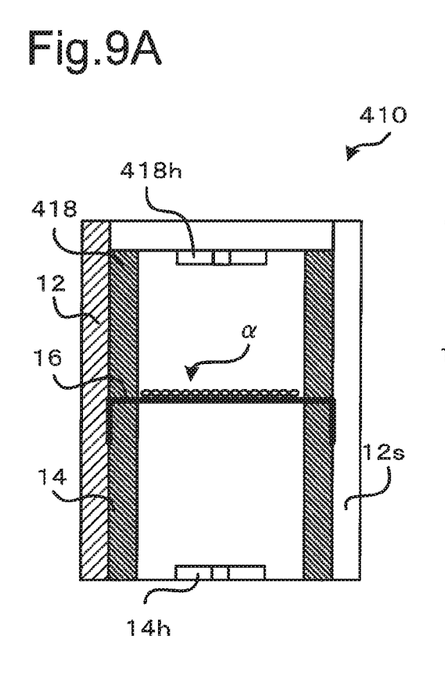
FIGS. 9A to 9C are sectional schematic diagrams illustrating the configuration of another cell culture device.
Figure 9B:
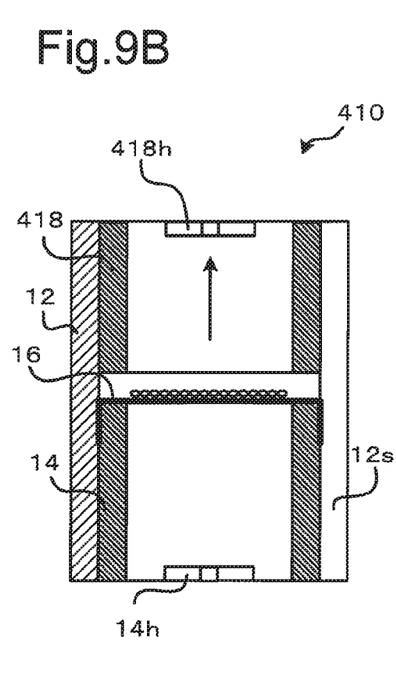
Figure 9C:
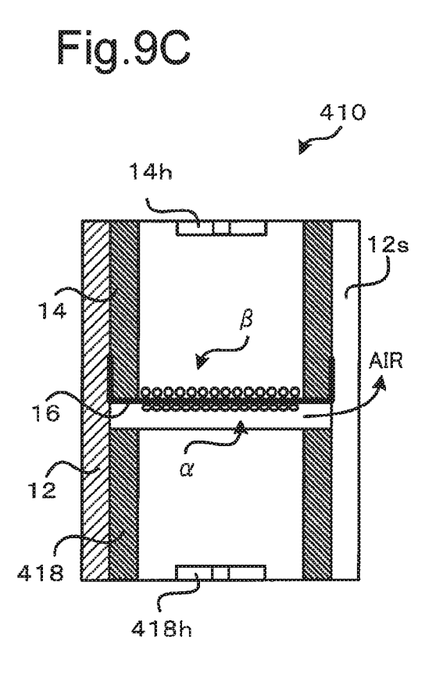

FIGS. 9A to 9C are sectional schematic diagrams illustrating the configuration of a cell culture device 410 according to a fifth embodiment of the disclosure. In the description below, the like components to those of the cell culture device 10 of the first embodiment are expressed by the like reference numbers and are not described in detail. The cell culture device 410 includes a second inner cylinder 418, in addition to an outer cylinder 12, a first inner cylinder 14 and a cell culture membrane 16.

The second inner cylinder 418 is placed to be laid on the first inner cylinder 14 such that their height directions are made identical with each other and to hold the cell culture membrane 16 placed between the end faces of the second inner cylinder 418 and the first inner cylinder 14. According to this embodiment, the outer cylinder 12 is not provided with the first grip portion 12h. A third grip portion 418h similar to the first grip portion 12h is provided at an end of the second inner cylinder 418 on a side away from the cell culture membrane 16.

FIG. 9A illustrates the state that cells α are seeded on one surface of the cell culture membrane 16 (surface exposed to inside of the second inner cylinder 418), like FIG. 1A. FIG. 9B illustrates the state that the second inner cylinder 418 is pulled up in the height direction (upward in the vertical direction) from the state of FIG. 9A to be away from the cell culture membrane 16. The second inner cylinder 418 may be readily pulled up by holding the third grip portion 418h. FIG. 9C is a state that the cell culture device 410 is turned upside down from the state of FIG. 9B and cells β are additionally seeded on the rear side of the culture surface of the cells α. The cell culture device 410 may be readily turned upside down by holding the third grip portion 418h and suspending and pulling up the cell culture device 410.

According to this embodiment, the second inner cylinder 418 is configured to be slid in the height direction inside of the outer cylinder 12 and held at the slid position by applying an upward force in the height direction to the second inner cylinder 418 with holding the outer cylinder 12. This configuration may be achieved by adjusting the relationship between the outer diameter of the second inner cylinder 418 and the inner diameter of the outer cylinder 12 in the state that the first inner cylinder 14 is placed inside thereof, the surface roughness of the inner wall surface of the outer cylinder 12 and the outer surface of the second inner cylinder 418, and the weight of the second inner cylinder 418.

This configuration also provides the above advantageous effect of readily holding the cell culture membrane 16 by the presence of the first slit 12s provided in the outer cylinder 12, like the first embodiment. Additionally according to the fifth embodiment, the second inner cylinder 418 is slid in the height direction to be away from the cell culture membrane 16, prior to inversion of the cell culture device 410. This causes the space immediately above the culture surface of the cell α to communicate with outside of the outer cylinder 12 through the first slit 12s of the outer cylinder 12. This accordingly enables the air remaining on the culture surface of the cells α to be readily removed through the first slit 12s, after inversion of the cell culture device 410. The state of air removal is shown by an arrow in FIG. 9C. This suppresses a problem caused by the air remaining on the culture surface of the cells α.

The total height of the first inner cylinder 14 and the second inner cylinder 418 is shorter than the height of the outer cylinder 12 according to this embodiment, but a different configuration may be employed. This may be any configuration that enables the second inner cylinder 418 to be held at a slid position even after inversion of the cell culture device 410. The second inner cylinder 418 may be held in the outer cylinder 12, for example, by means of engagement elements that are provided on the inner wall surface of the outer cylinder 12 and the outer surface of the second inner cylinder 418 to engage with each other, instead of using the frictional force between the outer cylinder 12 and the second inner cylinder 418. Using the frictional force is, however, desired in terms of repeated slidability of the second inner cylinder 418 at any arbitrary position.

F. Modifications

Modification 1

In the respective embodiments described above, the first slit 12s provided in the outer cylinder 12 is formed along the entire height of the outer cylinder 12. The first slit 12s may, however, be formed in a partial area in the height direction of the outer cylinder 12. Providing the first slit 12s at least in a position that overlaps with an end of the first inner cylinder where the cell culture membrane 16 is placed to be extended along the height direction of the outer cylinder 12 enables the holding force for holding the cell culture membrane 16 to be produced by placing the cell culture membrane 16 between the first inner cylinder and the outer cylinder 12.

In the configuration that the first slit 12s is provided only in the partial area in the height direction of the outer cylinder 12, for example, an insertion-side leading edge of the first inner cylinder 14 may be tapered to have the diameter reduced toward the leading edge, in order to facilitate insertion of the first inner cylinder 14 or the like into the outer cylinder 12. In another example, the outer diameter of the outer cylinder 12 may be made slightly larger in a remaining area of the outer cylinder 12 other than an area where the first slit 12s is provided than the outer diameter of the outer cylinder 12 in the area where the first slit 12s is provided, in order to facilitate insertion of the first inner cylinder 14 or the like into the outer cylinder 12.

Modification 2

Each of the grip portions provided in the outer cylinder 12, the first inner cylinder and the second inner cylinder is formed in a cross shape in the top view according to the above embodiments, but may be formed in a different shape. The grip portion may be formed in any shape that enables the cell culture device to be readily held, for example, a shape provided by linking different locations on an outer circumference of an opening at an end of an outer cylinder or at an end of an inner cylinder such as to cross the opening. The shape that enables a cell culture device to be held in the vicinity immediately above the center of gravity Un the vicinity on the axial line) of the cell culture device is especially preferable in terms of readily holding the cell culture device stably and readily suppressing an external stimulus (noise) on the cultured cells. At least part of the grip portions described in the respective embodiments may be omitted.

In terms of reducing an external stimulus on the cultured cells, it is preferable that the cell culture device is sunk in the culture solution. When the specific gravity of the cell culture device is not sufficiently large, it is preferable to provide a mechanism for holding the cell culture device in the state that the cell culture device is sunk in the culture solution.

Modification 3

Both the surfaces of the cell culture membrane are used for cell culture according to the above embodiments, but only a single surface of the cell culture membrane may be used for cell culture. In the latter case, there is no need that the respective surfaces of the cell culture membrane communicate with each other by means of the through holes. For example, a layer serving as the scaffold of cultured cells may be formed on a base plate that is, for example, a thin film of a resin such as PET. Even when the layer itself serving as the scaffold of cultured cells does not have sufficient elasticity or sufficient strength, there is only a need that the entire structure including the base plate has sufficient elasticity and sufficient strength such as to be folded down at an end of the first inner cylinder and placed and held between the first inner cylinder and the outer cylinder.

When the cell culture device is used for one-sided culture, there is no need to supply a suspension of cells to be seeded as a culture solution to the rear face of the cell culture membrane. Accordingly the cell culture membrane 16 may not be placed in the middle in the height direction of the outer cylinder 12 as described in the above respective embodiments but may be placed in the vicinity of the other end 14t of the outer cylinder 12.

Modification 4

The outer cylinder and the inner cylinder (first inner cylinder and second inner cylinder) are formed in the cylindrical shape according to the above respective embodiments but may have a different configuration. For example, the inner cylinder may be formed in a cylindrical shape, and the outer cylinder may be formed in a polygonal columnar shape (for example, hexagonal columnar shape or octagonal columnar shape) circumscribing the inner cylinder. In another example, the outer cylinder may be formed in a cylindrical shape, and the inner cylinder may be formed in a polygonal columnar shape inscribed in the outer cylinder. In another example, both the inner cylinder and the outer cylinder may be formed in polygonal columnar shapes. The outer surface of the inner cylinder and the inner wall surface of the outer cylinder may not be necessarily arranged to come into contact with each other over the entire circumferential direction, but may be arranged to come into contact with each other to such an extent that produces the sufficient holding force for holding the cell culture membrane.

The disclosure is not limited to any of the embodiments, the examples and the modifications described above but may be implemented by a diversity of other configurations without departing from the scope of the disclosure. For example, the technical features of any of the embodiments, the examples and the modifications corresponding to the technical features of each of the aspects described in Summary may be replaced or combined appropriately in order to solve part or all of the problems described above or in order to achieve part or all of the advantageous effects described above. Any of the technical features may be omitted appropriately unless the technical feature is described as essential herein.

REFERENCE SIGNS LIST 10, 110, 210, 310, 410 cell culture device
11 well
12 outer cylinder
12h first grip portion
12o, 12t end
12s first slit
14, 214 first inner cylinder
14h second grip portion
14o, 14t end
16 cell culture membrane
18, 318, 418 second inner cylinder
214c groove
214m, 318m membrane support
214s second slit
318s third slit
418h third grip portion

The invention claimed is:

1. A cell culture device, comprising:
a first inner cylinder formed in a tubular shape;
a cell culture membrane placed to cover over an entire first end of the first inner cylinder; and
an outer cylinder formed in a tubular shape, configured to place the first inner cylinder inside thereof such that a height direction of the outer cylinder is identical with a height direction of the first inner cylinder, and provided with a first slit overlapping with at least the first end of the first inner cylinder to be extended in the height direction, the first slit passing completely through the outer cylinder in a thickness direction of the outer cylinder, and the first slit being formed along the height direction in the entire outer cylinder.

2. The cell culture device according to claim 1, further comprising:
a second inner cylinder formed in a tubular shape such that a height direction of the second inner cylinder is identical with the height direction of the first inner cylinder and placed in the outer cylinder to come into contact with the first inner cylinder via the cell culture membrane on a side of the first end of the first inner cylinder.

3. The cell culture device according to claim 2,
wherein the second inner cylinder is configured to be slidable in the height direction in the outer cylinder by applying a force in the height direction and to be held at a slid position.

4. The cell culture device according to claim 1,
wherein the first inner cylinder includes:
a second slit provided at a position that overlaps with the first slit provided in the outer cylinder to be extended in the height direction from the first end of the first inner cylinder; and
a pair of membrane supports provided at positions which overlap with the first slit provided in the outer cylinder and between which the second slit is open at the first end of the first inner cylinder, such as to be extended outward in a radial direction of the first inner cylinder via the first slit to outside of the outer cylinder.

5. The cell culture device according to claim 1,
wherein the first inner cylinder has a concavo-convex shape that is provided at a position to come into contact with the cell culture membrane on an outer surface near to the first end of the first inner cylinder.

6. The cell culture device according to claim 1,
wherein the cell culture membrane is configured to be folded down toward an outer surface of the first inner cylinder along an outer circumference at the first end of the first inner cylinder, and
the cell culture membrane is placed and held between an inner wall surface of the outer cylinder and the outer surface of the first inner cylinder.

7. The cell culture device according to claim 1, wherein
the outer cylinder includes a first grip portion provided at an end of the outer cylinder that is nearer to the first end of the first inner cylinder out of two ends of the first inner cylinder, the first grip portion extends between different locations on an outer circumference of an opening at the end such as to cross the opening at the end of the outer cylinder, and
the first inner cylinder includes a second grip portion provided at a second end out of the two ends of the first inner cylinder, the second grip portion extends between different locations on an outer circumference of an opening at the other end of the first inner cylinder such as to cross the opening at the other end of the first inner cylinder.

8. The cell culture device according to claim 1,
wherein the outer cylinder includes a first grip portion provided at an end that is nearer to the first end of the first inner cylinder out of two ends of the first inner cylinder, the first grip portion extends between different locations on an outer circumference of an opening at the end such as to cross the opening at the end of the outer cylinder.

9. The cell culture device according to claim 8,
wherein the first grip portion is formed from two line segments that are arranged to cross each other on an axial line of the first inner cylinder.

10. The cell culture device according to claim 1,
wherein the first inner cylinder includes a grip portion provided at a second end out of the two ends of the first inner cylinder, the grip portion extends between different locations on an outer circumference of an opening at the second end such as to cross the opening at the other end of the first inner cylinder.

11. The cell culture device according to claim 10,
wherein the grip portion is formed from two line segments that are arranged to cross each other on an axial line of the first inner cylinder.

* * * * *